United States Patent
Franklin

[11] Patent Number: 5,869,321
[45] Date of Patent: Feb. 9, 1999

[54] THIN FILM CULTURE PLATE DEVICE CONTAINING GRANULATED MEDIUM PARTICLES

[75] Inventor: Gummadi J. Franklin, Arden Hills, Minn.

[73] Assignee: Minnesota Mining and Manufacturing Company, St. Paul, Minn.

[21] Appl. No.: 917,000

[22] Filed: Aug. 20, 1997

Related U.S. Application Data

[63] Continuation of Ser. No. 529,307, Sep. 18, 1995, abandoned.

[51] Int. Cl.[6] .............................. C12N 1/20; C12Q 1/04; C12Q 1/10; C12Q 1/06
[52] U.S. Cl. ........................ 435/253.6; 435/34; 435/38; 435/39; 435/252.1; 435/305.4; 435/309.1; 435/848; 435/849
[58] Field of Search .................. 435/4, 30, 34, 435/38, 39, 243, 248, 252.1, 253.6, 297.1, 299.1, 305.1, 305.4, 309.1, 810, 822, 848, 849

[56] References Cited

U.S. PATENT DOCUMENTS

| | | | |
|---|---|---|---|
| 3,202,731 | 8/1965 | Grevenstuk et al. | 264/7 |
| 4,071,412 | 1/1978 | Eisenberg et al. | 435/253.6 |
| 4,565,783 | 1/1986 | Hansen et al. | 435/299 |
| 4,755,468 | 7/1988 | Jung et al. | 435/178 |
| 5,089,413 | 2/1992 | Nelson et al. | 435/254 |
| 5,137,812 | 8/1992 | Matner | 435/38 |
| 5,232,838 | 8/1993 | Nelson et al. | 435/30 |
| 5,364,766 | 11/1994 | Mach et al. | 435/34 |
| 5,424,122 | 6/1995 | Crandall et al. | 428/355 |
| 5,435,851 | 7/1995 | Kasica et al. | 127/69 |
| 5,462,860 | 10/1995 | Mach et al. | 435/34 |
| 5,601,998 | 2/1997 | Mach et al. | 435/34 |

FOREIGN PATENT DOCUMENTS 0 398 703 A1  11/1990  European Pat. Off. ......... C12M 1/16

OTHER PUBLICATIONS

Derwent Publication, Japan 06 254 382, 13 Sep. 1994.

*Primary Examiner*—Leon B. Lankford, Jr.
*Assistant Examiner*—Christopher R. Tate

[57] ABSTRACT

The present disclosure reports a thin film culture plate device including i) a self-supporting, waterproof substrate containing a layer of a unique reconstitutable culture medium made of nutrients for growing microorganisms, and a mixture of gelling agents which are prepared in granular form by agglomerating the nutrients and mixture of gelling agents in the presence of an aqueous binder and ii) a cover sheet adhered to a portion of the substrate. Methods to make agglomerated medium particles are also reported.

14 Claims, 1 Drawing Sheet

THIN FILM CULTURE PLATE DEVICE CONTAINING GRANULATED MEDIUM PARTICLES

This application is a continuation of application No. 08/529,307, filed on Sep. 18, 1995, now abandoned.

This invention is generally related to thin film culture plate devices which are used to detect and enumerate bacteria which are present in a sample and particularly related to a thin film culture plate device which contains granulated medium particles made of nutrients and a mixture of gelling agents.

BACKGROUND

Classical methods for determining the presence and number of bacteria in a sample are time consuming, tedious and labor intensive. Typically, a technician must prepare reagents and nutrients, mix the nutrients with agar, heat the mixture, pour the mixture into a petri dish, allow the agar to gel, obtain a test sample, dilute the test sample, add an aliquot of the diluted sample to the agar, incubate the inoculated plate for 24–48 hours and finally count the number of growing bacterial colonies in the petri dish. Products and processes which reduce the preparation time and which facilitate a count of the bacterial colonies would clearly be welcomed by those working in this field.

One example of a product which greatly simplifies the above preparation time is a thin film culture plate device for growing microorganisms that is described in U.S. Pat. No. 4,565,783 as well as variations of this device such as those described in U.S. Pat. Nos. 5,089,413; 5,137,812 and 5,232,838. In a typical thin film culture plate device, a reconstitutable dry powder containing a gelling agent and microbial growth nutrients is coated on a waterproof substrate. A transparent, read-through cover sheet coated on a surface with an acrylate adhesive containing an indicator dye and powdered gelling agent is attached to the coated substrate.

When the above device is used, a predetermined amount of an aqueous sample is typically placed in contact with the coated substrate and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of bacterial colonies which are grown on the culture device. Thin film culture plate devices are commercially available and are sold under the tradename PETRIFILM plates by 3M, St. Paul, Minn.

Thin film culture plate devices are generally much simpler to use than conventional agar medium/petri dish systems because there is no need for the user to heat and mix the growth medium, agar and other reagents and then add the mixture to petri dishes or pour plates. In addition, these devices are compact and easily disposed of and therefore are easier and safer to use.

In spite of the many advantages that thin film culture plate devices have over conventional types of culture systems, the utility of these thin film plates for certain applications may be challenged under certain conditions, microbes and samples. For example, the limited amount of gelling agent in the device may be insufficient to remain in a semi-solid state when inoculated with certain samples containing some microorganisms. Briefly, some samples which contain certain bacteria commonly known as "liquifiers" will cause the growing colonies to overrun the semi-solid gel and thus hinder detection and enumeration of such microorganisms.

The present invention addresses the difficulties presented in attempting to grow, detect and enumerate a wide variety of microorganisms using thin film culture plate devices.

SUMMARY OF THE INVENTION

This invention provides a thin film culture plate device containing novel medium particles. The thin film culture plate devices of this invention have an expanded range of use for detecting and enumerating bacteria in bacteria-containing samples. In part, this invention is directed to a thin film culture plate device including i) a self-supporting, waterproof substrate containing a layer of a unique reconstitutable culture medium of nutrients for growing microorganisms and a mixture of gelling agents which are prepared in granular form by agglomerating the nutrients and mixture of gelling agents in the presence of an aqueous binder in a fluidized bed and ii) a cover sheet adhered to a portion of the substrate.

In one embodiment of this invention, the thin film culture plate device includes a substrate made of a film or sheet of polyester and a cover sheet made of a film or sheet of transparent polyethylene. In this embodiment, an agglomerated, particulate, reconstitutable culture medium or medium particles are adhered to the substrate and to the cover sheet with a nontoxic adhesive.

In yet another embodiment, the thin film culture plate device may optionally include a hydrophobic spacer adhered to a surface of the substrate which is adapted to retain an amount of a sample or a liquid in contact with the reconstitutable culture medium.

This invention also includes, in part, a method of making medium particles which includes the step of agglomerating nutrients for growing microorganisms and a mixture of gelling agents in the presence of an aqueous binder in a fluidized bed.

In a preferred embodiment of this invention, microbial nutrients such as proteins, carbohydrates and salts are combined with gelling agents such as xanthan, locust bean, and guar gums or mixtures thereof A preferred mixture of these materials includes about 15–25 wt. % nutrients and about 75–85 wt. % gelling agents. This mixture of the nutrients and gelling agents is initially contacted with a sufficient amount of an aqueous binder to form particles having particle diameters greater than about 40 microns and then further drying of the particles at a temperature less than about 40° C. provides medium particles having a moisture content of less than about 5 wt. %. Preferred medium particles prepared according to this method generally have particle diameters in the range of about 50–150 microns and particle densities in the range of about 0.5–0.6 g/cm$^3$.

Additional advantages and features which further characterize and describe the present invention are reported in the accompanying drawing and detailed description and are recited in the appended claims.

DETAILED DESCRIPTION

Figure 1:
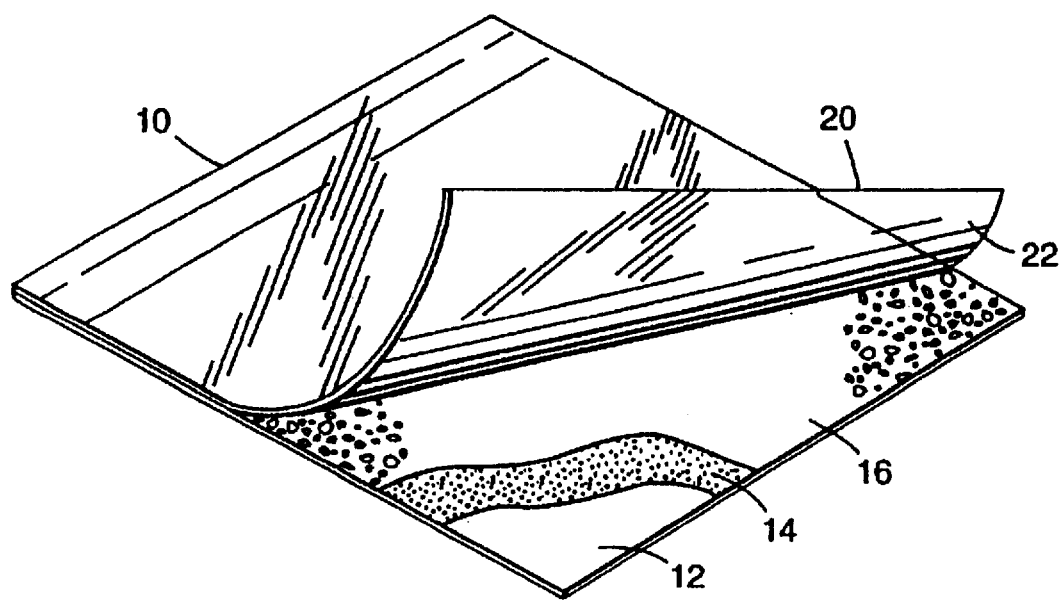
FIG. 1 is a top perspective view, partially in section, of a dry culture device used to grow microorganisms.

The present invention provides medium particles comprised of a granulated mixture of nutrient and gelling agents which provide certain advantages over known powdered media. The medium particles of this invention include known nutrients, gelling agents and reagents which are commercially available. A variety of nutrients may be used which include components such as carbohydrates, proteins and minerals. A preferred nutrient mixture may include standard nutrients reported in *Standard Methods for the Examination of Dairy Products.* 14th Edition, American Public Health Association, Washington, D.C. as well as other salts and minerals such as sodium pyruvate, monobasic potassium phosphate, and dibasic potassium phosphate.

A fluidized bed agglomerator is used to produce medium particles. In this process, powdered nutrients and gelling agents are mixed until homogeneous. The powders are agglomerated into relatively uniform granular particles in the presence of an aqueous binder in a fluidized bed. Typically, the binder will contain a dibasic phosphate salt such as the potassium or sodium salt. The buffer may also contain a magnesium salt, such as magnesium chloride. The binder spray is added to the powders in a controlled fashion to produce homogeneous agglomerates of nutrients and gelling agents. The agglomerates are dried in the fluidized bed.

In a particularly preferred embodiment, the xanthan gum, locust bean gum, and guar gum powders are combined in the ratio of 2 to 2 to 1. Persons skilled in the art will recognize that this ratio may be varied in other culture plate formats. In addition, blends of other natural and synthetic hydrocolloid materials or gelling materials including carrageenan may be used.

Traditionally, these plates could be disinfected only with ethylene oxide, which did not kill all the naturally occuring contaminants, such as the "liquifiers". It is thought that the binder spray aids the gums in cross-linking. It is this cross-linking which allows the medium to be exposed to gamma radiation, because if the media is not cross-linked the gamma radiation will break down the gum.

The output specifications of the media particles include that at least 70% of the particles be in the range of 325 to 140 mesh, and that the moisture be less than 5%.

The medium particles may be applied by any means suitable for the application of a substantially uniform layer. Preferred methods include the use of a shaker-type device, or the use of a powder coater.

FIG. 1 illustrates a thin film culture plate device suitable for use with the medium particles of the present invention. Briefly, these types of devices are described in U.S. Pat. No. 4,565,783 and U.S. Pat. No. 5,089,413 both of which describe processes of making and using these types of thin film culture plate devices.

The thin film culture plate device 10 includes a body member having a self-supporting, waterproof substrate 12. Substrate 12 is preferably a relatively stiff material made of a waterproof material that does not absorb water such as polyester, polypropylene, or polystyrene. For example, polyester films approximately $100\mu$ to $180\mu$ thick, polypropylene films approximately $100\mu$ to $200\mu$ thick, and polystyrene films approximately $300\mu$ to $380\mu$ thick have been found to work well with the present invention. Other suitable substrates include paper with a polyethylene or other substantially water-proof coating, such as "Schoeller Type MIL" photoprint paper (Schoeller, Inc., Pulaski, N.Y.). In addition, substrate 12 can be transparent, translucent, or opaque, depending on whether one wishes to view and count microorganism colonies through substrate 12.

The upper surface of substrate 12 is coated with a layer of adhesive 14 and then further coated with reconstitutable culture medium particles 16 of this invention. The adhesive should be sufficiently transparent when hydrated to allow viewing of bacterial colonies growing on the surface of the substrate through the coated substrate.

The adhesive should also be coated on the substrate in a thickness which allows the substrate to be uniformly coated with medium particles without completely embedding the medium particles in the adhesive. Suitable adhesives are coated (preferably, knife-coated) onto substrate 12 at a thickness that is preferably less than the diameter of the medium particles 16 adhered to adhesive layer 14. Typically, enough adhesive composition is used to facilitate adherence of the medium particles to upper surface 14 of substrate 12, but not so much that the particles become completely embedded in the layer of adhesive. Generally, an adhesive coating weight of about 0.15 g/24 square inches or higher (dry coating weight) is suitable.

The adhesive composition preferably is a pressure-sensitive adhesive. More preferably, the adhesive is a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer may be a lower alkyl ($C_2$ to $C_{10}$) ester monomer of acrylic acid, including, without limitation, isooctyl acrylate (IOA), 2-ethylhexyl acrylate, butyl acrylate, ethyl acrylate, isoamyl acrylate, and mixtures of these monomers, while the alkyl amide monomer may be, without limitation, acrylamide (ACM), methacrylamide, N-vinylpyrrolidone (NVP), N-vinylcaprolactam (NVCL), N-vinyl-2-piperidine, N-(mono- or di-lower alkyl ($C_2$ to $C_5$))(meth)acrylamides, N-methyl(meth)acrylamide, N,N-dimethyl(meth)acrylamides, or mixtures these monomers. Suitable water-insoluble adhesive copolymers include a copolymer of IOA and ACM, or an aqueous emulsion suspension of a copolymer of IOA and NVP, as described in U.S. Pat. No. 5,232,838. Alternative adhesives may include an adhesive formed by aqueous emulsion polymerization as described in U.S. Pat. No. 5,424,122.

Appropriate adjustments to the pH of the adhesive are made, as needed, to insure that the adhesive compositions are non-inhibitory to the growth of microorganisms. Typically, the pH of the adhesive should be maintained at a pH of about 5 to 9, more preferably at a pH of about 6 to 8.

In a preferred thin film culture device, the amount of sample used (or to be evaluated) is contained on the substrate by the components of the medium alone. In an alternate embodiment, a device may include a sample-containing foam layer. A foam spacer, not shown, having a circular opening in the foam is adhered to the medium coated surface of substrate 12. The foam spacer which covers the periphery of substrate 12 defines the area which is to be inoculated with a sample and serves to prevent the sample from leaking from the substrate. Suitable materials for the spacer member are any solid non-inhibitory natural or synthetic substance which is readily available in sheet form but is not a microorganism growth site. Polyethylene, polypropylene, polyethylene terephthalate and polystyrene are a few examples of suitable synthetic materials. In particular, relatively inexpensive commercially available polystyrene foams and polyethylene foams are preferred, and polystyrene foam is presently most preferred. Natural substances such as cellulose sheets, metal e.g. foil sheets, wood and the like are suitable alternatives.

A cover sheet 20 is attached to one edge of an upper surface of substrate 12. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene.

In a manner similar to coating adhesive and medium particles on a surface of substrate 12, a surface of cover sheet 20 is also coated with adhesive and reconstitutable culture medium particles. In a preferred embodiment, the layer of adhesive 22 includes an indicator dye to aid detection and enumeration of growing bacterial colonies.

Generally, cover sheet 20 will have the same properties, such as transparency and preferred water impermeability, as substrate 12. Furthermore, cover sheet 20 may have imprinted patterns or a mask-edge (not shown) to aid in the counting of microorganism colonies, to provide a target for placement of the aqueous test sample, and/or for aesthetic reasons.

Cover sheet 20 may be selected to provide the amount of oxygen transmission necessary for the type of microorganism desired to be grown. For example, polyester films have a low oxygen permeability (less than 0.78 g/100 cm$^2$/24 hours per 25$\mu$ of thickness), and would be suitable for growing anaerobic bacteria. On the other hand, some forms of polyethylene have a relatively high oxygen permeability (approximately 78 g/100 cm$^2$/24 hours per 25$\mu$ of thickness), and would be suitable for the growth of aerobic organisms, with or without the use of an air permeable membrane. One preferred material for cover sheet 20 is a 1.6 mil biaxially-oriented polypropylene film. Another preferred material for the cover sheet is a commercially available polyethylene terephthalate treated with an antifog agent (commercially available as FSI-47 from Film Specialties Inc., Whitehouse, N.J.). Another preferred material is sol-gel treated polyethylene terephthalate (commercially available as SCOTCHPAR Brand film No. FE 40492 from 3M, St. Paul, Minn.). The cover sheet 20 may be affixed by conventional methods such as heat sealing, adhesives, double coated adhesive tapes and the like.

Suitable indicator dyes for use in the present invention include compounds which are metabolized by the growing organisms and which become colored due to the action of the metabolites produced by developing bacterial colonies. The visual change in color allows for easier detection and visualization of the growing colonies. Preferred indicator dyes include reduction sensitive dyes such as triphenyltetrazolium chloride, p-tolyl tetrazolium red, tetrazolium violet, veratryl tetrazolium blue and related dyes. Other suitable dyes include dyes which are sensitive to pH changes such as neutral red.

Triphenyltetrazolium chloride is a preferred dye for use in devices designed to culture bacteria which may be found in food products such as S. aureus, Micrococcus, or other types of bacteria which may be commonly found in food products such as milk or other dairy products.

In use, a predetermined amount of inoculum, typically about one milliliter of inoculum, is added to the device illustrated in FIG. 1 by pulling back cover sheet 20 and adding an aqueous test sample or water to the middle of substrate 12. Cover sheet 20 is then replaced over substrate 12 and the inoculum is evenly spread on the substrate. A convenient tool to do this spreading is a weighted circular template which also is used to confine the inoculum to a specific area of substrate 12. As the inoculum contacts and is spread on substrate 12, the culture medium on substrate 12 hydrates to form a growth-supporting nutrient gel. The inoculated device is then incubated for a predetermined time after which the number of bacterial colonies growing on the substrate may be counted through the transparent cover sheet 20.

Although the use of the medium particles of this invention on a thin film device is described above, those of ordinary skill in the art will recognize that the medium particles may be used in other culturing devices which are known in the art.

The following examples are intended to provide further details and embodiments related to the practice of the present invention. These examples are provided for illustrative purposes and should not be construed to limit the scope of the present invention which is defined in the appended claims.

EXAMPLES

Example 1

Three pre-weighed powders, 12.7 kilograms of xanthan gum (KTLTF, available from Kelkco. Co.), 12.7 kilograms of locust bean gum (GENU, available from Hercules) and 6.4 kilograms of re-extracted guar gum (available from Rhone-Poulenc) were placed into the loading bowl of a 60 kilogram capacity Glatt fluid bed agglomerator to produce medium particles. The fluid bed agglomerator was fitted with silicone gaskets and a filter sock with a 2 micron nominal pore size. The fluid bed agglomerator was cycled for 30 seconds to facilitate mixing of these powders and then 8.0 kilograms of standard methods nutrients, including sugars, proteins, and salts (available from Acumedia Inc.) was added to the loading bowl. Again, the fluid bed agglomerator was cycled for another 30 seconds of mixing.

3.5 liters of a dilute phosphate buffer binding spray solution made according to the Standard Methods, containing potassium phosphate and magnesium chloride, were loaded to the spray pump of the fluid bed agglomerator. The machine blower, heater, and spray pump were started at the same time.

The binding spray solution was added at the rate of 10 milliliters per 3 minutes per kilogram of powder, through a top-mounted spray port of 1.5 millimeters in diameter. All the binding spray solution was added in the first 25–30 minutes of the 55–65 minute total cycle time.

The specifications of the resulting medium particles included at least 70% of the particles in the range of 325 to 140 mesh which had less than 5 wt. % moisture content.

The following table shows the temperature, percent moisture, and density (grams per cubic centimeter) of the product, the amount of diluent added, and the elapsed time.

| Temp. of Product °C. | Total Diluent (ml) | Time (min.) | Moisture | Density |
|---|---|---|---|---|
| 23 | | | | |
| 23 | 400 | 5 | | |
| 22 | 750 | 10 | | |
| 24 | 1100 | 15 | | |
| 27 | 1500 | 18 | | |
| 28 | 2500 | 20 | | |
| 28 | 2500 | 23 | | |
| 29 | 3000 | 26 | | |
| 30 | 3500 | 29 | | |
| 31 | | 35 | | |

-continued

| Temp. of Product °C. | Total Diluent (ml) | Time (min.) | Moisture | Density |
|---|---|---|---|---|
| 33 | | 45 | | |
| 34 | | 55 | 8.3 | .51 |
| 35 | | 60 | | |
| 36 | | 65 | 5.1 | .57 |

Example 2

A silicone coated paper web approximately 4–5 mils thick with a grid pattern printed on the side opposite the silicone coating (available from Schoeller Technical Papers) was coated at a coating weight of about 0.15 grams per 24 square inches (dry coating weight) with a solution of isooctyl acrylate/acrylamide adhesive and then dried. The adhesive was coated on the side with the preprinted grid; that is, on the side opposite the side coated with the silicone.

Medium particles were made by the fluid bed agglomeration process of Example 1 and these medium particles were coated onto the adhesive layer by passing the paper web through a cloud of suspended medium particles. The medium particles which contacted the adhesive adhered to the coated paper web, and the excess medium particles were shaken off the web. The coating weight of media particles was approximately 0.4 grams per 24 square inches. This coating was substantially water-free and cold-water reconstitutable.

A second web of transparent polypropylene was coated with a solution of the isooctyl acrylate/acrylamide adhesive at a coating weight of about 0.15 grams per 24 square inches (dry coating weight). This adhesive contained the indicator dye triphenyl tetrazolium chloride. Medium particles were coated at approximately 0.4 grams per 24 square inches onto the adhesive layer of the polypropylene web in the same manner as the medium particles were coated onto the silicone coated paper. The polypropylene was substantially bacteria and water vapor impermeable.

The two webs were brought together, with the sides coated with medium particles facing each other. A rectangle 3 inches by 4 inches was cut out from the combined webs, and the webs were then heat-sealed together along one edge in a hinge-like fashion.

Example 3

A stock phosphate buffer solution was prepared by dissolving 34 grams of monobasic potassium phosphate in approximately 500 milliliters of microbiologically suitable (MS) water in a one liter volumetric flask. The pH was adjusted to 7.2 with 1N sodium hydroxide, and MS water added to bring to volume. The stock buffer was sterilized by autoclaving at 121° C. for 15 minutes. Storage was at 0° C. Working phosphate buffer (hereinafter referred to simply as phosphate buffer) was prepared by adding 1.25 milliliters stock buffer to MS water in a one liter volumetric flask and diluting to the mark. The phosphate buffer was autoclaved at 121° C. for 15 minutes.

Eleven grams of fresh, raw milk were added to 99 milliliters phosphate buffer solution to prepare the initial 1:10 dilution. Samples were mixed by shaking the diluted samples 25 times in an arc of approximately 30 centimeters in 7 seconds. Diluents are preferably at about the same temperature as the sample in order to avoid additional stress to bacteria that are present.

From the initial 1:10 dilutions, serial 10-fold dilutions were made by transferring 11 milliliters of well-mixed, diluted sample to 99 milliliters diluent. Samples of dilutions of $10^{-2}$ and $10^{-3}$ were used.

Standard methods agar (available from BBL Co.) was prepared according to the manufacturer's direction. The standard methods agar was autoclaved for 15 minutes at 121° C. The agar was then placed in a water bath to allow the agar to reach a temperature of 45° C. in order to melt and temper the agar. One milliliter of the appropriately diluted sample was pipetted into each of the petri dishes. 10 to 12 milliliters of melted, tempered agar was then poured into each petri dish. As each dish was poured, the dish was swirled gently to mix the sample and agar and to distribute the mixture evenly across the plate. The agar was allowed to solidify. The plate was then inverted and incubated for 45–48 hours at 32° C.

Standard aerobic count PETRIFILM plates (catalog No. 6400, 3M, St. Paul, Minn.) as well as the plates made in Example 2 were also used to test appropriately diluted samples. For both of these plates, the top clear film of the plate was lifted and one milliliter of diluted sample was pipetted onto the center of the bottom film. The top film was allowed to drop onto the inoculum. A plastic spreader was placed, recessed side down, over the center of the sample. The sample was dispersed by pressing on the center of the spreader. The gel was allowed to solidify, and the plates were then inverted and incubated for 45–48 hours at 32° C.

The colonies were counted after the incubation time with a Quebec colony counter. Counts ranging from 15 to 300 were used to calculate the mean raw counts for each milk-medium combination except when the plate had counts of 15 or less (samples 14 and 30, Table 1). One sample, number 9, was "too numerous to count" on all plates, and so was discarded.

Results from 30 fresh, raw milk samples are shown in the following table. These counts are averages of two duplicates.

| Sample | Log of Dil. | Agar | Control | Lot 001 | Lot 002 |
|---|---|---|---|---|---|
| 1 | 3 | 202 | 170 | 109 | 115 |
| 2 | 2 | 53.5 | 96 | 109.5 | 90.5 |
| 3 | 2 | 12 | 23 | 24.5 | 31 |
| 4 | 2 | 60 | 59 | 63 | 59 |
| 5 | 3 | 102 | 144 | 141.5 | 136 |
| 6 | 2 | 55.5 | 64.5 | 74.5 | 68.5 |
| 7 | 2 | 49.5 | 79 | 83 | 67 |
| 8 | 2 | 30.5 | 31.5 | 39.5 | 28.5 |
| 9 | tntc | tntc | tntc | tntc | tntc |
| 10 | 2 | 23 | 22.5 | 26.5 | 28.5 |
| 11 | 3 | 71.5 | 102 | 181.5 | 75.5 |
| 12 | 3 | 132 | 169.5 | 144.5 | 155.5 |
| 13 | 2 | 45 | 74.5 | 71 | 72 |
| 14 | 2 | 8 | 12 | 10 | 11.5 |
| 15 | 3 | 105 | 216.5 | 209 | 188.5 |
| 16 | 2 | 48.5 | 67.5 | 57.5 | 62 |
| 17 | 3 | 29.5 | 44.5 | 43.5 | 37 |
| 18 | 2 | 47 | 58 | 84 | 99.5 |
| 19 | 2 | 25 | 29.5 | 23.5 | 32 |
| 20 | 2 | 21 | 19.5 | 31.5 | 22.5 |
| 21 | 2 | 262.25 | 213.7 | 290.3 | 255.7 |
| 22 | 2 | 14.5 | 13.5 | 20.5 | 23.5 |
| 23 | 2 | 82 | 122.5 | 105.5 | 105 |
| 24 | 2 | 34.5 | 42.5 | 60 | 57.5 |
| 25 | 2 | 15 | 18 | 24.5 | 28.5 |
| 26 | 2 | 85.5 | 85 | 72.5 | 70.5 |
| 27 | 3 | 68 | 93.5 | 89 | 69.5 |
| 28 | 3 | 105.5 | 145.5 | 118 | 134.5 |
| 29 | 3 | 137.5 | 133.5 | 114.5 | 122 |
| 30 | 2 | 8.5 | 6.5 | 12 | 6.5 |

I claim:

1. A method of making a relatively uniform population of medium particles comprising the steps of (a) agglomerating nutrients for growing microorganisms and a mixture of gelling agents in the presence of a sufficient amount of an aqueous binder spray to form particles comprising nutrients and a mixture of gelling agents and having diameters greater than about 40 microns; and (b) drying said particles at a temperature less than about 40° C. until said particles have a moisture content of less than about 5 wt. %, wherein said nutrients are selected from the group consisting of proteins, carbohydrates, salts and mixtures thereof and said mixture of gelling agents comprises xanthan gum, locust bean gum, and quar gum in a weight ratio of 2:2:1, respectively.

2. The method of making the medium particles of claim 1 wherein the nutrients are selected from the group consisting of pancreatic digest of casein, yeast extract, beef extract, glucose, dibasic potassium phosphate, monobasic potassium phosphate, sodium pyruvate and mixtures thereof.

3. The method of making the medium particles of claim 1 further comprising the step of collecting particles having a diameter in the range of about 50–150 microns and a density in the range of about 0.5–0.6 g/$cm^3$.

4. The method of making the medium particles of claim 1, wherein at least 70% of said particles have diameters in a range of about 50–150 microns, and the moisture content of said particles is less than 5%.

5. A reconstitutable culture medium comprising a relatively uniform population of agglomerated particles, wherein each said particle comprises about 15–25 wt. % nutrients and about 75–85 wt. % of a mixture of gelling agents, wherein said nutrients are selected from the group consisting of proteins, carbohydrates, salts and mixtures thereof and said mixture of gelling agents comprises xanthan gum, locust bean gum, and quar gum in a weight ratio of 2:2:1, respectively, and wherein at least 70% of said particles have diameters in a range of about 50–150 microns and the moisture content of said particles is less than about 5 wt. %.

6. The reconstitutable culture medium of claim 5 wherein the nutrients are selected from the group consisting of pancreatic digest of casein, yeast extract, beef extract, glucose, dibasic potassium phosphate, monobasic potassium phosphate, sodium pyruvate and mixtures thereof.

7. The reconstitutable culture medium of claim 5 wherein each said particle comprises about 20 wt. % nutrients and about 80 wt. % gelling agents.

8. The reconstitutable culture medium of claim 5, wherein said culture medium is sterilizable with gamma radiation while retaining gelling agent integrity.

9. A thin film culture plate device for growing microorganisms comprising 1) a self-supporting, waterproof substrate containing a layer of a reconstitutable culture medium of claim 5 and 2) a cover sheet adhered to a portion of the substrate.

10. The device of claim 9 wherein the substrate is a sheet of polyester.

11. The device of claim 9 wherein the cover sheet is a film of transparent polyethylene.

12. The device of claim 9 further comprising a hydrophobic spacer adhered to a surface of the substrate adapted to retain an amount of liquid in contact with the reconstitutable culture medium.

13. The device of claim 9 wherein the reconstitutable culture medium is adhered to the substrate with a nontoxic adhesive.

14. The thin film culture plate device of claim 9, wherein said device is sterilizable with gamma radiation while retaining gelling agent integrity.

* * * * *